United States Patent [19]

Toth et al.

[11] Patent Number: 4,508,926

[45] Date of Patent: Apr. 2, 1985

[54] 4-HYDROXY-BENZHYDROLS, PROCESS FOR THEIR PREPARATION AND PHARMACEUTICAL COMPOSITIONS CONTAINING THEM

[75] Inventors: Edit Toth; Jozsef Torley; Gyorgy Fekete; László Szporny; Laszlo Vereczkey; Eva Pàlosi; Imre Klebovich; Pal Vittay; Sandor Gorog; Istvan Hajdu, all of Budapest, Hungary

[73] Assignee: Richter Gedeon Vegyeszeti Gyar Rt., Budapest, Hungary

[21] Appl. No.: 565,840

[22] Filed: Dec. 27, 1983

[30] Foreign Application Priority Data

Dec. 28, 1982 [HU] Hungary ............... 4188/82

[51] Int. Cl.³ .......................................... C07C 39/11
[52] U.S. Cl. ........................... 568/766; 568/744; 568/745; 568/765; 568/775; 568/809; 568/811; 568/812
[58] Field of Search ............... 568/744, 745, 764, 763, 568/765, 766, 775, 809, 811, 812, 716

[56] References Cited

U.S. PATENT DOCUMENTS

| 2,247,404 | 7/1941 | Perkins et al. | 568/745 |
| 2,719,866 | 10/1955 | Gerzon | 568/744 |
| 3,943,122 | 3/1976 | Sailor | 568/622 |
| 4,094,908 | 6/1978 | Toth et al. | 568/809 |

*Primary Examiner*—Werren B. Lone
*Attorney, Agent, or Firm*—Karl F. Ross; Herbert Dubno

[57] ABSTRACT

The invention relates to new 4-hydroxy-benzhydrols of the formula (I)

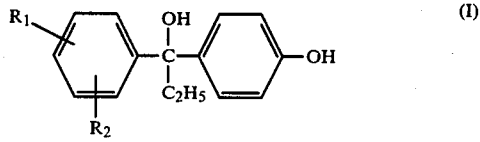

wherein $R_1$ and $R_2$ independently represent hydrogen, halogen, trihalomethyl, alkyl having from one to 4 carbon atoms or alkoxy having from one to 4 carbon atoms, with the proviso that if $R_1$ is hydrogen, $R_2$ is other than hydrogen or a 3-trifluoromethyl group, or if $R_1$ is a 2-methyl group, $R_2$ is other than a 5-methyl group.

According to another aspect of the invention there are provided processes for the preparation of these compounds.

The compounds of the formula (I) are pharmacologically active. In particular, they are suitable for the treatment of acute ethanolic intoxication. Pharmaceutical compositions containing them as active ingredients are also within the scope of the invention.

4 Claims, No Drawings

4-HYDROXY-BENZHYDROLS, PROCESS FOR THEIR PREPARATION AND PHARMACEUTICAL COMPOSITIONS CONTAINING THEM

The invention relates to new 4-hydroxy-benzhydrols, processes for their preparation and pharmaceutical compositions containing these compounds as active ingredient.

More particularly, the invention concerns new 4-hydroxy-α-ethyl-benzhydrol derivatives of the formula (I)

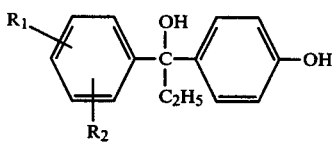

wherein
$R_1$ and $R_2$ independently represent hydrogen, halogen, trihalomethyl, alkyl having from one to 4 carbon atoms or alkoxy having from one to 4 carbon atoms, provided that if $R_1$ is hydrogen, $R_2$ is other than hydrogen or a 3-trifluoromethyl group, or if $R_1$ is a 2-methyl group, $R_2$ is other than an 5-methyl group.

The term "halogen" as used herein embraces all of the halogens, and may be fluorine, chlorine, bromine or iodine, preferably fluorine, chlorine or bromine.

The term "alkyl having from one to 4 carbon atoms" refers to straight or branched chained aliphatic hydrocarbon groups containing from one to 4 carbon atoms.

The term "alkoxy having from one to 4 carbon atoms" is used herein to refer to straight or branched chained alkoxy groups containing from one to 4 carbon atoms.

The trihalomethyl groups may contain any of the halogens listed above, preferably fluorine.

Compounds of analogous structure are for example disclosed in the following references: C.A. 22, 410[1]; 35, 1781[2]; 40, 4712[5]; 42, P 1015 b; 47, 9548 e; 50, 12390 c; 50, 2509 i; 55, 17915 e; 55, 15413 b; 75, P 103682 b; 76, P 119921 k; 82, 16477 g; 90, 86082 g; 92, 52927 b. None of these citations does, however, mention any pharmaceutical activity of the disclosed compounds.

According to a further aspect of the invention there is provided a process for the preparation of the compounds of the formula (I), wherein $R_1$ and $R_2$ each have the same meanings as defined above, which process comprises (a) reacting 4'-hydroxy-propiophenone with an organometallic compound of the formula (II)

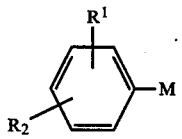

wherein
$R_1$ and $R_2$ are as defined above,
M is an alkali metal, preferably lithium, sodium or potassium, or an MgX group, in which
X is halogen; or (b) reacting a benzophenone of the formula (III)

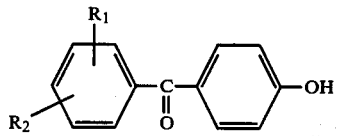

wherein $R_1$ and $R_2$ are as defined above, with an organometallic compound containing an ethyl group, preferably an ethyl magnesium halide or ethyl lithium; or (c) reducing a compound of the formula (IV)

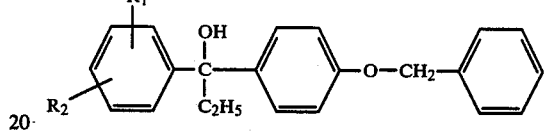

wherein $R_1$ and $R_2$ are as defined above.

The starting compounds are known or can be prepared by methods known in the art. The compounds of the formula (II) may for example be obtained by preparing Grignard reactants from the corresponding substituted aryl halides by methods known in the art (see e.g. M. S. Kharash et al.: Grignard reactions of nonmetallic substances, Ed., Prentice-Hall Inc. (1954) 5–90), while the alkali metal-organic compounds are prepared as described in Houben-Weyl: Methoden der Organischen Chemie, XIII/1, 134–159, 389–405 (1970).

The hydroxy-ketones of the formula (III) may for example be synthesized by the Fries reaction (A. H. Blatt: The Fries Reaction in Organic Reactions, I, 342). The starting compounds of the formula (IV) can for example be prepared by reacting 4-benzyloxypropiophenone with the corresponding substituted phenyl magnesium halides, for example following the procedure described by M. S. Kharash et al. (Grignard Reactions of Nonmetallic Substances, Ed., Prentice-Hall Inc. (1954) 138–143).

According to a preferred embodiment of process variant (a) 4-hydroxy-propiophenone is reacted with an at least two-equimolar amount of an organometallic compound of the formula (II), in a dry inert organic solvent, preferably in inert gas atmosphere. As an organometallic compound preferably a substituted phenyl lithium, preferably a substituted phenyl magnesium halide, e.g. chloride or bromide is employed. The reaction is carried out in an aprotic organic solvent, e.g. hexamethylphosphoric amide, dimethyl sulfoxide, aliphatic and cycloaliphatic ethers such as diethyl ether, di-n-butyl ether, ethyleneglycol dimethyl ether, dioxane, tetrahydrofuran, aliphatic and aromatic hydrocarbons such as ligroin, benzene, toluene, xylene, or in a mixture of these solvents. As an inert gas for example nitrogen or argon can be used. The reaction temperature may range from −70° C. up to the boiling point of the solvent, and preferably is between −40° C. and 100° C. When the reaction is complete, the reaction mixture is decomposed for example with a dilute aqueous mineral or organic acid such as sulfuric acid, hydrochloric acid, acetic acid, or preferably with an aqueous solution of ammonium chloride, and the obtained compound of the formula (I) is isolated. The product can for example be purified by chromatography or recrystallization.

Process variant (b) is preferably carried out by reacting a benzophenone of the formula (III) with at least two molar equivalents of an ethyl magnesium halide or ethyl lithium in an inert organic solvent, preferably in inert gas atmosphere. As an ethyl magnesium halide preferably ethyl magnesium iodide or bromide is employed in the reaction. The reaction is accomplished in the solvents and at the temperatures described in connection with process variant (a), for example in nitrogen or argon atmosphere. The product is generally isolated as described above.

According to process variant (c) a compound of the formula (IV) is reduced. The reductive splitting of the benzyl group is preferably carried out by catalytic hydrogenation. As a catalyst metals such as ruthenium, palladium, platinum, nickel, iron, copper, cobalt, zinc, molybdenum, wolfram, etc. and oxides and sulfides of these metals can be employed. The catalysts may be prepared by reducing their stable oxides with hydrogen, directly in the reaction vessel. This procedure is especially suitable for the preparation of a finely dispersed platinum or palladium catalyst. The catalytic hydrogenation may be accomplished also in the presence of catalysts precipitated on the surface of a carrier, e.g. charcoal, silica, alumina or sulfates or carbonates of alkali earth metals. The reaction may be carried out also in the presence of a Raney-nickel catalyst, in an organic solvent inert under the reaction conditions. As a solvent for example lower aliphatic alcohols, ethers, esters, aliphatic, cycloaliphatic and aromatic hydrocarbons or mixtures of these solvents may be employed. The hydrogenation may be carried out under atmospheric or higher pressure, preferably not exceeding 506.6 kPa, at a temperature between 20° C. and the boiling point of the solvent employed. The reduction is preferably carried out at room temperature, under atmospheric pressure until ceasing of the hydrogen uptake. The catalyst is then filtered off, the filtrate is evaporated, and if desired, the product is purified e.g. by distillation or crystallization.

The new compounds of the formula (I) possess valuable pharmacological properties. More particularly, they are suitable for the treatment of acute ethanolic intoxication, therefore can be widely used in therapy. Acute ethanolic intoxication is characterized in euphoria, general stimulation, ataxia, somnolence, paralytic condition, etc. The dangers of this toxic, pathological condition are well known and cannot be neglected, since the intoxicated person is a threat to his environment (e.g. driving while intoxicated) and exposes his own health to danger. Acute alcoholic intoxication is a substantial "risk factor" of cerebral ischaemic infarcts (Hillbom, M. et al: Lancet 2, 1181 (1978); Stroke 12, 422 (1981)). Ethanolic intoxication has no satisfactory antidote. α-Methyl-para-tyrosine normalizes the ethanolic locomotoric hyperactivity on mice in a dose range, in which it decreases the spontaneous locomotoric activity of animals (Carlsson, A. et al.: Psychopharm., 26, 307, 1972). The narcotizing effect of alcohol is reduced by stimulants but these agents prolong the motoric incoordination (ataxia) (Wallagsen, H. et al.: Actions of alcohol, Amsterdam, Elsevier, 1970; Rech, R. H. et al.: Ann. N.Y. Acad. Sci. 28, 426, 1976; Todzy et al.: Psychopharm, 59, 143, 1978). The alcoholic intoxication, narcosis is shortened by L-cysteine (Sprince, H. et al.: Agents and Actions, 4, 125, 1974; Nagasawa, H. T. et al.: Life Sci., 17, 707, 1975), which is used as a reference compound for alcoholic narcosis period tests.

The change of ethanolic narcosis period was tested on Hann.-Wistar rats of both sexes weighing 160 to 180 g. each, which were fasted for 16 hours prior to treatment. The animals were treated with various doses of the compounds of the formula (I) in groups of ten, orally, One hour after treatment the rats were treated with 3.5 mg./kg. of ethanol intraperitoneally (i.p.). The narcosis period of the animals was measured from the elapse of the righting reflex until a spontaneous correction of the body position. The average of the narcosis period and the percentage difference from the control were calculated. The results are shown in Table 1.

Abbreviations:

$\bar{x} \pm S.E.$ = average value ± standard error n = number of animals

The control group was treated with placebo and 3.5 mg./kg. of ethanol.

Narcosis period of the control: $92.4 \pm 4.83$ ($\bar{x} \pm S.E.$) min.

A = 2-trifluoromethyl-4'-hydroxy-α-ethyl-benzhydrol

B = 3-chloro-4'-hydroxy-α-ethyl-benzhydrol

TABLE 1

| Compound | Dose (mg./kg.) | Ethanolic narcosis period $\bar{x} \pm S.E.$ | n |
|---|---|---|---|
| A | 5.0 | 69 ± 4.5 | 10 |
|  | 20.0 | 52 ± 6.0 | 10 |
|  | 40.0 | 39 ± 3.4 | 10 |
| B | 40.0 | 60 ± 7.5 | 10 |
| L-cysteine | 500.0 | 63 ± 4.2 | 10 |
|  | 1000.0 | 66 ± 5.9 | 10 |
| Control | — | 100 ± 5.2 | 10 |

As appears from the above results, the compounds of the formula (I) effectively shorten the ethanolic narcosis period, their effect (unlike that of L-cysteine) is dose-dependent, and is superior or at least equal to the effect of L-cysteine in considerably smaller doses.

The acute toxicity of the compounds according to the invention was determined on Hann.-Wistar rats of both sexes, weighing 160 to 180 g. each, which had been treated with a single 500 mg./kg. dose of the test compounds, orally. The animals were observed for 14 days after treatment. The percentage of the perished animals is given in Table 2.

TABLE 2

| Compound (500 mg./kg.) | Perished animals (%) | n |
|---|---|---|
| A | 0 | 10 |
| B | 0 | 10 |

The toxicity of the test compounds is low especially when compared to the effective doses; accordingly, the compounds have a very favorable therapeutic index.

The central nervous activities of the compounds according to the invention were examined on mice and rats with the following methods: electroshock (Swinyard, E. A., Brown, W. C., Goodman, L. S.: J. Pharmacol. Exp. Ther. 106, 319 (1952)); metrazole spasm (Everett, G. M., Richards, R. K.: J. Pharmacol. Exp. Ther. 81, 402 (1944)), thiosemicarbazide spasm (Da Venzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J. Pharmacol. Exp. Ther. 132, 360 (1961)), nicotine spasm (Stone, C. A., Mecklenburg, K. L., Torhans, M. L.: Arch. Int. Pharmacodyn. 117, 419 (1958)), rotarod test (Kinnard, W. C., Carr, C. J.: J. Pharmacol. Expt. Ther. 121, 254 (1957)), physostigmine lethality preventing effect (Nose, T., Kojima, M.: Europ. J. Pharmacol. 10, 83 (1970)), yohimbine potentiation effect (Quinton, R. M.: Brit. J. Pharmacol. 21, 51 (1963)), and analgesic activity (Bianchi, G., Franceschini, J.: Brit. Pharm. Chemother. 9, 280 (1954)).

The compounds of the formula (I) when tested by the above methods were completely ineffective even in a dose of 160 mg./kg.

The pharmacologically active compounds according to the invention can be used in therapy in the form of pharmaceutical compositions which are formulated as preparations suitable for oral, rectal and/or parenteral administration. For oral administration tablets, dragées or capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectin or formaldehyde casein, etc. The formulations may also contain adhesives and lubricants such as talc, colloidal silica, stearin, calcium or magnesium stearate, etc.

Tablets are prepared for example by wet granulation and subsequent pressing. A mixture of the active ingredient and the vehicle and optionally a part of the disintegrating agent are granulated with an aqueous, alcoholic or aqueous-alcoholic solution of the excipients in a suitable equipment, and the granules are dried. The remaining portion of the disintegrating substance, lubricant, antiadhesive or optional further additives is then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragées, using protecting, flavouring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories, which contain in addition to the active ingredients a carrier mass, called adeps pro suppository. Suitable carriers include vegetable fats, e.g. hardened vegetable oils, triglycerides of fatty acids having from 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable solution, the active ingredient is dissolved in distilled water and/or various organic solvents, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents, such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 0.1 and 300.0 mg./kg., preferably 2.0 and 160.0 mg./kg., preferably in more smaller dose units.

The invention will be further described with reference to the following illustrative Examples.

EXAMPLE 1

3-Chloro-4'-hydroxy-α-ethyl-benzhydrol

To a Grignard reactant prepared from 14.6 g. of magnesium turnings and 115 g. of 3-chloro-bromobenzene in 350 ml. of dry tetrahydrofurane a solution of 30.1 g. of 4'-hydroxy-propiophenone in 540 ml. of dry tetrahydrofurane is added dropwise, with stirring under slight reflux. The reaction mixture is slightly boiled for 30 additional minutes, cooled and decomposed by pouring onto a mixture of ice and glacial acetic acid. After separation the organic phase is washed with a saturated sodium chloride solution, dried over anhydrous magnesium sulfate, and the solvent is distilled off under reduced pressure. Crystallization of the solid residue from a mixture of n-hexane and ethyl acetate yields 42.6 g. of the named compound, melting at 132° to 134° C.

Analysis for $C_{15}H_{15}ClO_2$: Calculated: C 68.57%, H 5.75%, Cl 13.49%; Found: C 68.66%, H 5.57%, Cl 13.71%.

EXAMPLE 2

4-Fluoro-4'-hydroxy-α-ethyl-benzhydrol

To a solution of ethyl lithium prepared from 2.8 g. of lithium metal and 21.8 g. of ethyl bromide in 265 ml. of dry ether a solution of 10.8 g. of 4-fluoro-4'-hydroxy-benzophenone in 50 ml. of dry tetrahydrofurane is added dropwise, with stirring in argon atmosphere, at a temperature between −40° C. and −30° C. When the addition is complete, the mixture is allowed to warm up to 0° C., and is then stirred at this temperature for further 30 minutes. The mixture is decomposed with a 20% aqueous ammonium chloride solution under cooling. The aqueous phase is extracted with ether, the ethereal phases are combined, washed to neutral with water, and dried over anhydrous magnesium sulfate. The solution is evaporated under reduced pressure, and the solid residue is crystallized from a mixture of n-hexane and ethyl acetate to yield 8.2 g. of the named product, melting at 125° to 126° C.

Analysis for $C_{15}H_{15}FO_2$: Calculated: C 73.15%, H 6.14%, F 7.71%; Found: C 73.26%, H 6.18%, F 7.95%.

EXAMPLE 3

4-Chloro-4'-hydroxy-α-ethyl-benzhydrol

To a solution of ethyl magnesium bromide prepared from 3.9 g. of magnesium turnings and 17.4 g. of ethyl bromide in 50 ml. of dry ether a solution of 9.3 g. of 4-chloro-4'-hydroxy-benzophenone in 40 ml. of dry ether is added dropwise, with stirring at −10° C., in nitrogen atmosphere. The reaction mixture is allowed to warm up to room temperature, stirred at this temperature for an additional half an hour, and is then poured onto a solution of ammonium chloride in ice water under cooling. The aqueous phase is extracted with ether, the ethereal phases are combined, washed to neutral with water, and dried over anhydrous magnesium sulfate. After filtering the solvent is distilled off in vacuo, the residue is decolored with charcoal in methanol, the solution is filtered, and the solvent is evaporated under reduced pressure. The crude mixture is crystallized from a mixture of benzene and ethyl acetate to yield 5.5 g. of the named compound, melting at 148° to 149° C.

Analysis for $C_{15}H_{15}ClO_2$: Calculated: C 68.75%, H 5.75%, Cl 13.49%; Found: C 68.78%, H 5.87%, Cl 13.57%.

EXAMPLE 4

4-Bromo-4'-hydroxy-α-ethyl-benzhydrol

To 400 ml. of a 0.5 molar ethereal 4-bromophenyllithium solution a solution of 7.5 g. of 4'-hydroxy-propiophenone in 37 ml. of dry tetrahydrofurane is added dropwise, with stirring at a temperature between −50° C. and −40° C. The reaction mixture is stirred at 0° C. for an additional hour, and is then decomposed with a mixture of ice and glacial acetic acid. The aqueous phase is extracted with ether, the ethereal phases are combined, and washed to neutral with water. After drying over anhydrous magnesium sulfate the solvent is distilled off under reduced pressure, and the residue is chromatographed on a silica gel column with a 7:3 mixture of benzene and ethyl acetate as an eluting agent. The solvent is distilled off in vacuo, and the residue is crystallized from a mixture of ethyl acetate and dichloromethane. 4.2 g. of the named compound are obtained, melting at 161° to 162° C.

Analysis for $C_{15}H_{15}BrO_2$: Calculated: C 58.64%, H 4.92%, Br 26.01%; Found: C 58.86%, H 4.83%, Br 26.17%.

EXAMPLE 5

4-Trifluoromethyl-4'-hydroxy-α-ethyl-benzhydrol 27 g. of 4-trifluoromethyl-4'-benzyloxy-α-ethyl-benzhydrol are dissolved in 270 ml. of benzene, and the solution is hydrogenated in the presence of 13.5 g. of a 10% palladium-on-charcoal catalyst. When the uptake of the calculated amount of hydrogen is complete (about 80 minutes), the catalyst is filtered off, benzene is distilled off under reduced pressure, and the residue is crystallized from a mixture of ethyl acetate and n-hexane. 19 g. of the named compound are obtained, melting at 126° to 127° C.

Analysis for $C_{16}H_{15}F_3O_2$: Calculated: C 64.88%, H 5.10%, F 19.24%; Found: C 64.68%, H 5.23%, F 19.50%.

Similarly there can be prepared the following compounds by proper selection of the starting substances:

2-Methoxy-4'-hydroxy-α-ethyl-benzhydrol, melting point: 165° to 166° C.

Analysis for $C_{16}H_{18}O_3$: Calculated: C 74.39%, H 7.02%; Found: C 74.46%, H 7.11%.

2-Trifluoromethyl-4'-hydroxy-α-ethyl-benzhydrol, melting point: 131° to 132° C.

Analysis for $C_{16}H_{15}F_3NO_2$: Calculated: C 64.86%, H 5.10%, F 19.28%; Found: C 64.97%, H 5.16%, F 19.35%.

EXAMPLE 6

Preparation of pharmaceutical compositions

| Tablets | |
|---|---|
| Composition of a single tablet: | |
| active ingredient | 100.0 mg. |
| lactose | 184.0 mg. |
| potato starch | 80.0 mg. |
| polyvinyl pyrrolidone | 8.0 mg. |
| talc | 12.0 mg. |
| magnesium stearate | 2.0 mg. |
| aerosil (colloidal silica) | 2.0 mg. |
| ultraamylopectin | 12.0 mg. |

From the ingredients 400-mg. tablets are prepared by wet granulation and subsequent pressing. Active ingredient: 2-trifluoromethyl-4'-hydroxy-α-ethyl-benzhydrol.

Dragées

Tablets as described above are coated with a layer prepared from sugar and talc in a known manner. Dragées are polished with a mixture of bee wax and carnauba wax. Weight of a dragée: 500.0 mg.

| Capsules | |
|---|---|
| Composition of a capsule: | |
| active ingredient | 50.0 mg. |
| lactose | 100.0 mg. |
| talc | 2.0 mg. |
| potato starch | 30.0 mg. |
| cellulose (microcrystalline) | 8.0 mg. |

The active ingredient is thoroughly admixed with the additives, the mixture is passed through a 0.32-mm. sieve, and filled into gelatine capsules size 4.

Active ingredient: 2-trifluoromethyl-4'-hydroxy-α-ethyl-benzhydrol

| Suppositories | |
|---|---|
| Composition of a suppository: | |
| active ingredient | 100.0 mg. |
| lactose | 200.0 mg. |
| basic substance (e.g. Witepsol H) | 1700.0 mg. |

The basic substance is melted and then cooled to 35° C. The active ingredient is thoroughly admixed with the lactose, and the mixture is homogenized in the basic substance in a suitable equipment. The obtained mass is filled into cool molds. One suppository weights 2000 mg.

Active ingredient: 2-trifluoromethyl-4'-hydroxy-α-ethyl-benzhydrol.

| Suspensions | |
|---|---|
| Composition of 100 ml. of suspension: | |
| active ingredient | 1.0 g. |
| sodium hydroxide | 0.26 g. |
| citric acid | 0.30 g. |
| nipagin (4-hydroxy-benzoic acid methylester sodium salt) | 0.10 g. |
| Carbopol 940 (polyacrylic acid) | 0.30 g. |
| ethanol (96%) | 1.00 g. |
| raspberry aroma | 0.60 g. |
| sorbite (70% aqueous solution) | 71.00 g. |
| distilled water ad | 100.0 ml. |

To a solution of nipagin and citric acid in 20 ml. of distilled water Carbopol is added in small portions, with vigorous stirring, and the solution is allowed to stand for 10 to 12 hours. Thereafter the solution of the above amount of sodium hydroxide in 1 ml. of distilled water is added dropwise, followed by dropwise addition of an aqueous solution of sorbite and an ethanolic raspberry aroma solution, with stirring. Active ingredient is added in small portions, and the mixture is homogenized. The suspension is supplemented with distilled water to 100 ml., and the suspension syrup is passed through a colloidal mill.

Active ingredient: 3-chloro-4'-hydroxy-α-ethylbenzhydrol.

We claim:

1. A 4-Hydroxy-α-ethyl-benzhydrol compound of the formula (I)

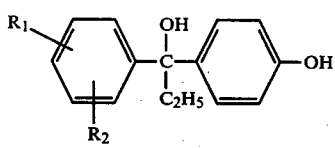

wherein $R_1$ and $R_2$ independently represent hydrogen, halogen, trihalomethyl, alkyl having from one to 4 carbon atoms or alkoxy having from one to 4 carbon atoms, but when $R_1$ is hydrogen, $R_2$ is other than hydrogen or a 3-trifluoromethyl group, or when $R_1$ is a 2-methyl group, $R_2$ is other than an 5-methyl group.

2. A compound selected from the following group:
3-chloro-4'-hydroxy-α-ethyl-benzhydrol,
4-fluoro-4'-hydroxy-α-ethyl-benzhydrol,
4-chloro-4'-hydroxy-α-ethyl-benzhydrol,
4-bromo-4'-hydroxy-α-ethyl-benzhydrol,
4-trifluoromethyl-4'-hydroxy-α-ethyl-benzhydrol,
2-methoxy-4'-hydroxy-α-ethyl-benzhydrol, and
2-trifluoromethyl-4'-hydroxy-α-ethyl-benzhydrol.

3. A pharmaceutical composition containing a 4-hydroxy-α-ethyl-benzhydrol derivative of the formula (I) as claimed in claim 1, wherein $R_1$ and $R_2$ are as defined in claim 1, as active ingredient, together with a pharmaceutically acceptable carrier and/or auxiliary substance.

4. A method of treating acute ethanolic intoxication in a subject which comprises administering to said subject an effective amount of a compound as defined in claim 1.

* * * * *